United States Patent [19]

Ashby

[11] 4,281,146

[45] Jul. 28, 1981

[54] METHOD OF NEUTRALIZING A HALOGEN SILICONE COMPOUND

[75] Inventor: Bruce A. Ashby, Schenectady, N.Y.

[73] Assignee: General Electric Company, Waterford, N.Y.

[21] Appl. No.: 107,248

[22] Filed: Dec. 26, 1979

[51] Int. Cl.$^3$ .......................... C07F 7/04; C07F 7/08; C07F 7/20

[52] U.S. Cl. .................................. 556/456; 556/452; 556/453; 556/457; 556/470

[58] Field of Search ............... 556/470, 452, 453, 456, 556/457

[56] References Cited

U.S. PATENT DOCUMENTS 2,698,861  1/1955  Shorr ..................................... 556/470

Primary Examiner—Paul F. Shaver
Attorney, Agent, or Firm—E. Philip Koltos; J. L. Young; Philip L. Schlamp

[57] ABSTRACT

A method of neutralizing a halogen silicone compound comprising adding to the halogen silicone compound an orthoformate and an alcohol so as to form an alkyl chloride and a formate which can then be distilled off.

14 Claims, No Drawings

METHOD OF NEUTRALIZING A HALOGEN SILICONE COMPOUND

BACKGROUND OF THE INVENTION

The present invention relates to neutralization processes and more particularly the present invention relates to the neutralization process of halogen silicone compounds generally and more specifically, chlorosilanes.

Fluorosilicone compounds are well known. Such compounds have the advantage of solvent resistance and they are utilized to form rubber parts or elastomeric parts where the parts come in contact with very solubilizing solvents. In particular such fluorosilicone compounds also include fluorosilicone fluids having a viscosity varying from 50 to 1,000,000 centipoise at 25° C. where the fluorosilicone fluids are utilized as hydraulic fluids as fluorosilicone greases and channel sealants. The fluorosilicone greases and channel sealants have the advantage of solvent resistance as mentioned previously.

In the past, it was usual to make the fluorosilicone fluids by equilibrating fluorosilicone substituted cyclic trisiloxane with low molecular weight, triorganosilyl end-stopped chainstoppers in the presence of alkali metal hydroxides or more preferably, a strong acid. The resulting mixture equilibrated to form a linear fluoro-substituted diorganopolysiloxane polymer having a viscosity of anywhere from 50 to 1,000,000 centipoise at 25° C. However, there was one disadvantage of the equilibration process and particularly because the low molecular weight triorganosilyl end-stopped chainstoppers would go into the polymer only very slowly such that there resulted a formation of high amounts of cyclics at the terminal point of the equilibration reaction. Accordingly, the yield of the triorganosilyl end-stopped diorganopolysiloxane fluid was not as high as desired. There has been developed an improvement to such a process as disclosed in the patent application of Ben A. Bluestein entitled "Process for Synthesizing Silanol End-Stopped Fluorosilicone Fluid," Ser. No. 92,800 and as disclosed in the patent application of Ben A. Bluestein entitled "Process for Producing M-Stopped Silicone Fluids From Silanol Fluids," Ser. No. 92,920 which are incorporated into the present case by reference. These dockets disclose a novel way for producing a triorganosilyl end-stopped linear diorganopolysiloxane fluid. The process disclosed comprises taking an appropriate fluorosubstituted cyclotrisiloxane and reacting it with small amounts of water as a chainstopper, in the presence of an alkali metal hydroxide catalyst and polyethylene glycol dimethyl ether as a promotor. The process results in the formation of a linear silanol end-stopped diorganopolysiloxane polymer of a viscosity of 50 centipoise to 1,000,000 centipoise at 25° C. in very rapid fashion and at a very high yield. After the desired polymer has been formed, which may take place any where from 1 to 6 hours, the catalyst is neutralized with a suitable acidic agent such as a chlorosilane or a silyl phosphate as disclosed in the foregoing patent applications. The resulting silanol end-stop polymer is then taken and is reacted with a triogranohalogensilane which is preferably a triorganochlorosilane so as to chainstop or replace the silanol groups in the polymer with triorganosilyl groups. This reaction also results in high yield of the desired product. There is only one difficulty with this process and that is, it is desirable to use excess triorganochlorosilane so as to insure that all the silanol groups are terminated or replaced by triorganosilyl chainstopping groups. This causes another disadvantage in that excess chlorosilane is difficult to remove from the fluid. If it is not removed from the fluid, it makes the fluid acidic and causes it to revert or degrade upon standing. Accordingly, the excess halogen silane has to be neutralized to less than 50 and preferably less than 10 parts per million of acid. As disclosed in the foregoing patent applications, an alkali metal hydroxide is not desirable since it creates undesirable salts which might require filtration. Also, there could be utilized to neutralize the halogen silicone compound or chlorosilane soda ash and water as disclosed in the above patent applications. Although such an addition of soda ash and water would neutralize the chlorosilane, it creates a precipitate which has to be filtered out which filtration step is not necessarily desirable in many plant operations. Alkali metal hydroxide could be utilized, however, that creates alkali metal salts in the polymer which tend to degrade it under certain conditions. Accordingly, it is highly desirable to convert the excess chlorosilane to species wherein the chloride could be removed from the polymer by distillation at elevated temperature.

It should be noted that while the above neutralization process was mentioned or discussed in terms of production of fluorosilicone fluids such neutralization of chlorosilanes can be present or necessarily desirable in many silicone manufacturing operations. Accordingly, although the necessity in the neutralization step of excess chlorosilanes was mentioned above with respect to chlorosilanes in the production of fluorosilicone fluids, it must be understood that such a neutralization step may be necessary in any silicone process in which excess chlorosilanes are present and in which it is necessary to neutralize the excess chlorosilanes. Accordingly, if it is desired for one reason or another to neutralize the excess chlorosilanes, then it is desirable to utilize a neutralization step which will neutralize the chlorosilanes without requiring a filtration step and without the formation of inorganic salts which would degrade the final product as well as be difficult to separate from the final product.

It is known that orthoformates react with chlorosilanes to produce alkylchlorides, alkylformates and alkoxysilanes all in the same reaction. It is also known that catalysts such as aluminum chloride and zinc chloride are useful and necessary for completing these reactions. However, in the case where the final product is a polymer or a residue as described above, it is not desirable to utilize these metal chlorides with orthoformates to effect conversion of excess chlorosilanes to distillable species because of the deleterious effects of the metal chloride on the polymer or residue.

Accordingly, it is one object of the present invention to provide a process for neutralizing excess halogen silicone compounds.

It is an additional object of the present invention to provide a process for neutralizing or removing excess chlorosilanes so as to produce species which may be distilled off with degrading the polymer.

It is yet an additional object of the present invention to provide a novel process for neutralizing excess chlorosilanes in the production of fluorosilicone polymers.

These and other objects of the present invention are accomplished by means of the disclosure set forth herein below.

SUMMARY OF THE INVENTION

In accordance with the objects, there is provided by the present invention a method of neutralizing a halogen silicone compound comprising adding to the halogen silicone compound from 1 to 5 moles per mole of the halogen silicone compound of a formate of the formula,

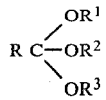

where R is selected from the class consisting of alkyl radicals of 1 to 3 carbon atoms and $R^1$, $R^2$, $R^3$ may be the same or different and are alkyl radicals of 1 to 8 carbon atoms and from 0.05 to 1 mole based on 1 mole of said halogen silicone compound of an aliphatic alcohol having 1 to 6 carbon atoms. This neutralization step or process may be applied with advantage as the terminal step in the production of fluorosilicone fluids by first the production of a silanol end-stopped diorganopolysiloxane fluids by the reaction of cyclic trisiloxanes with water in the presence of certain promoters and catalysts and then the silanol end-stopped fluid is reacted with a triorganohalogen silane and more specifically a triorgano chlorosilane. An excess of triorganochlorosilane is utilized to remove the silanol groups from the fluids and results in excess chlorosilane in the fluid mixture which makes the fluid acidic and would tend to cause the degradation of fluid if the fluid is allowed to remain in an acid state. Accordingly, desirably, the acidity of the fluid is lowered to below 50 parts per million by soda ash and water or more desirably and then filtering the salts out or more desirably by adding the formate of the formula shown above in combination with an aliphatic alcohol so as to form species which can be distilled off from the fluid. For a fuller understanding of the scope of the instant invention, reference is made to the discussion below.

DESCRIPTION OF THE PREFERRED EMBODIMENT

The present neutralization procedure or process can be applied to the neutralization of silicone halogen compound including silanes and siloxanes. Accordingly, if in the process mixture there is present excess chloropolysiloxanes so as to make the mixture acidic, the excess chloropolysiloxane can be neutralized with the procedure of the present process. Accordingly, the process of the present case applies to the neutralization of halogen polysiloxane and halogen silanes both of which come under the description of a halogen silicone compound. In addition, halogen groups other than chlorine may be neutralized by the process of the present case. However, since the chlorine group is the predominant halogen group in silicone compounds, it is likely that it will be chlorine silicone compound that will be neutralized or will be desired to be neutralized in silicone processes in accordance with the instant invention. However, it should be noted that the instant process is not limited to the neutralization of solely chlorine compounds, that there can be neutralized bromosilanes, and idosilanes as well as chloropolysiloxane, bromopolysiloxanes, and idopolysiloxanes. Accordingly, the process of the instant case has broader application then the preferred embodiment described below.

The preferred embodiment that will be described below indicates one area of where the present neutralization procedure can be utilized with advantage. In accordance with the description of the present invention, there will be described not only the preferred process, but the entire process for producing a triorganosilyl end-stopped diorganopolysiloxane polymer which has fluoropropyl substitute groups and which has a viscosity varying from 50 to 1,000,000 centipoise at 25° C. or more preferably has a viscosity varying from 50 to 100,000 centipoise at 25° C.

Accordingly, there will be described the preliminary steps for obtaining such a polymer or a fluid. In accordance with the preferred process for obtaining such materials as disclosed by the foregoing patent applications set forth in the background of the invention, there is taken 3,3,3-trifluoropropyl substituted dichlorosilane and hydrolyzed in water. After the hydrolysis reaction is completed and the excess acid is stripped off, the silocane hydrolyzate is taken, into it there is added a catalyst such as from 0.1 to 5 percent by weight of an alkali metal hydroxide such as potassium hydroxide and the resulting mixture is heated at elevated temperatures above 100° C. and more preferably above 150° C., for a period of time varying from 6 to 24 hours so as to preferentially distill overhead the cyclictrisiloxane. It should be noted that in the hydrolysis mixture there is present cyclopolysiloxane from $C_2$ to $C_{10}$ so when the mixture is heated with an alkali metal hydroxide catalyst there will be formed many types of cyclic polysiloxane; but by heating the mixture at the boiling temperature of the cyclotrisiloxane, the cyclotrisiloxane will distill off and will be removed from the hydrolysis mixture as it is formed so as to maximize the yield of such trisiloxane from the hydrolysis mixture. The cyclotrisiloxane is then taken and then is added the required amounts of water and from 50 to 500 per million of an alkali metal hydroxide catalyst.To such a reaction mixture, it is also added a catalyst promotor, a polyethylene glycol dimethylether. There is utilized from 0.1 to 2.0 parts of the polyethylene glycol dimethylether promotor per 100 parts of the cyclotrisiloxane and 0.02 to 5.0 parts of water per 100 parts of the cyclotrisiloxane as disclosed in the foregoing patent application of Ben A. Bluestein. The resulting mixture is then heated at temperature of 25° C. to 100° C. for 1 to 6 hours to preferentially form in high yield silanol end-stopped diorganopolysiloxane polymer having 3,3,3-trifluoropropyl substituted groups. The metal hydroxide is then neutralized with a strong acid such as hydrochloric acid, a silyl phosphate, or chlorosilane, to yield a substantially neutral mixture or mixture that does not have alkalinity or acidity that exceeds 10 parts per million. The composition is then heated at elevated temperatures, that is, temperatures above 100° C. to strip excess cyclics that may be present in the polymer so as to result in 95 percent yield of a silanol end-stopped diogranopolysiloxane polymer having 3,3,3-trifluoropropyl substituent groups and having a viscosity varying from 50 to 1,000,000 centipoise at 25° C.

Such a base polymer can be utilized as a base polymer in the production of one-component room temperature vulcanizable silicone rubber composition and two-component room temperature vulcanizable silicone rubber compositions. However, if desired to produce a triorganosilyl end-stopped diorganopolysiloxane polymer of a viscosity of 50 to 1,000,000 centipoise at 25° C., more preferably of 50 to 100,000 centipoise at 25° C. The fluid is then taken and per mole of the fluid there is added to it at least 2 moles of a triorgano silyl halogen silane. More specifically, a triorganochlorosilane is added to the reaction mixture so that the chlorine groups will react with silanol groups to liberate hydrogen chloride and append the substitute triorganosilyl groups for the silanol groups at the end of the polymer chain. This process which is an addition-condensation process takes place in 1 to 6 hours and is preferably carried out at a temperature of 0° to 100° C. and more preferably at temperatures of 50° to 100° C. After the chlorosilane has been added on to the end of the polymer, the composition is heated at 50° to 100° C. so as to strip overhead excess hydrogen chloride, and as much excess chlorosilane as possible, preferably with a nitrogen purge. It should be noted that the addition of the chlorosilane is preferably carried out at substantially anhydrous conditions, otherwise the chlorosilane will hydrolyze with water to produce silanol groups. It is preferred that the chlorosilane react directly with a silanol group at the end of the polymer chain of the linear fluid so as to condense out or add on the triorganosilyl groups at the end of the polymer chain in place of the silanol groups. Accordingly, the addition condensation reaction is completed and as much of the excess of HCL that has been formed is stripped off that can be stripped off. At this point, the acidity of the mixture is 3000 parts per million or less and the composition is ready for the neutralizing process of the instant case. It should be noted that neutralization of the instant case be applied to the neutralization of the chlorosilane and chlorosiloxanes from whatever process. After the acidity in the fluid has been reduced to 3,000 parts per million or less by stripping the halogen acid and excess chlorosilane, it cannot be reduced further by this procedure. It should also be appreciated that it is necessary to reduce the acidity to 50 parts per million or less since excess acidity in the polymer will tend to cause the polymer to revert to cyclopolysiloxanes upon long standing. Also the electrical properties of fluid will not be as good as would be desired with a high amount of acid in it. Accordingly, it is desirable to reduce the acidity to below 50 or to below 10 parts per million of acid. This may be accomplished by the adding of soda ash and water as disclosed in the foregoing Ben A. Bluestein patent applications. However, such a procedure forms salts which have to be filtered out before they could be used or utilized further. This additional filtration is expensive and time consuming and may not be desired in certain processing operations in the process for forming such fluids at silicone plants. In a manner of speaking, the plant of the present invention, such a filtration process was not desirable. Accordingly, the present neutralization procedure was devised. Accordingly, per one mole of the halogen silicone compound of the excess chlorosilane there is utilized anywhere from 1 to 5 moles of the formate of the formula of Formula (1) and more specifically from 1 mole to 2 moles per mole of the excess chlorosilane and from 0.05 to 1 mole of an aliphatic alcohol per mole of the chlorosilane. The aliphatic alcohol has from 1 to 6 carbon atoms and is more preferably methanol. In the formula of the formate, R is preferably selected from hydrogen and alkyl radicals of 1 to 3 carbon atoms, most preferably being methyl, $R^1$, and $R^2$, and $R^3$ may be the same or different alkyl radicals of 1 to 8 carbon atoms and most preferably methyl. Accordingly, the two most preferable neutralization ingredients in the process of the instant case are methanol and methylorthoformate. The methylothorformate and the methanol or aliphatic alcohol are added to the fluid and the fluid is subjected to elevated temperatures of 0° to 100° C. or more preferably heating temperatures of 50° to 100° C. so as to complete the reaction of the excess chlorosilane with the methylorthoformate and the methanol in a period of time varying from 1 to 6 hours, more preferably varying from 1 to 4 hours. The acidity of the mixture can be tested peridically to determine if it is less than 50 parts per million. When the acidity has been reduced to below 50 parts per million, then the reaction is over and the neutralization mixture can be cooled if desired. Preferably the neutralization procedure is carried out at atmospheric pressure since sub-atmospheric or super-atmospheric pressure produces no advantages. It is preferable to strip off the excess orthoformate and the other reaction products. To accomplish this, the mixture can be heated under vacuum or atmospheric pressure at temperatures not exceeding 200° C. so as to distill off the volatile materials. It should be noted that the triorganochlorosilane that is added to the silanol end-stop diorganopolysiloxane polymer to produce the triorganosilyl end-stopped polysiloxane fluid preferably has the formula,

$$R_3{}^7SiCl$$

where $R^7$ is a monovalent hydrocarbon radical, most preferably as alkyl radical of 1 to 8 carbon atoms on a 3,3,3-trifluoropropyl radical and preferably a mixture of such radicals and the foregoing process may be utilized with advantage to neutralize the excess chlorosilane that results from the addition of triorganochlorosilane to silanol end-stopped diorganopolysiloxane fluids so as to form a triogranosilyl end-stopped diorganopolysiloxane fluid having a viscosity varying from 50 to 1,000,000 centipoise at 25° C. wherein the acidity of the fluid is reduced to less than 50 parts per million. It should be noted that the process of the instant case can be preferably applied to process set forth in the preferred embodiment of the process of forming a triorganosilyl end-stopped diorganopolysiloxane fluid which is fluoropropyl substituted since it has been found that the present neutralization process is applied to such a fluid forming process with advantage, that is it does not require a filtration step and reduces the acidity of the fluid to the required level so it can be utilized as a basic fluid for surfactants in antifoam applications and in the formation of greases and channel sealants.

After the material is neutralized and preferably the resulting fluid can be heated to temperatures in excess of 150° C. to vent off undesired volatiles from the fluid before it is packaged or sent to finishing operations by which it is meant it can be utilized to form grease, channel sealants, antifoams, and other compositions. The fluid at this point is ready to be utilized as a final polymer fluid and is advantageously produced in a very high yield by the preferred process set forth below and as disclosed in the foregoing Ben A. Bluestein patent applications in conjunction with the instant application. It should be noted that this process is advantageously utilized to remove residual chlorosilanes and halogen silanes in a broader aspect from higher boiling materials, and more specifically, higher boiling alkoxy silanes such as phenylalkoxysilanes because of the low boiling points of the reaction products.

The instant neutralization process can also be used in removing residual chlorosilane from:
1. Trimethylsiloxy-terminated polymer which has been prepared by the reaction of silanol-terminated polydimethylsiloxanes and trimethylchlorosilane.
2. Alkoxy-terminated polysiloxanes which have been prepared by the reaction of α,ω-chlorosilyl-terminated polysiloxanes with either orthoformates or with alcohols.
3. Silanol-terminated polymers which have been prepared by the hydrolysis of α,ω-chlorosilyl-terminated polysiloxanes.
4. Higher-boiling alkoxysilanes.

The examples below are given for the purpose of illustrating the present invention. The examples below are not given for any purpose for setting limits and boundaries to the scope of the instant invention. All parts in the Examples are by weight.

EXAMPLE 1

To 400 parts of silanol end-stopped dimethyl 3,3,3-trifluoropropyl polysiloxane fluid having the viscosity of 675 to 725 centipoise at 47° C., which was heated to 47° C., there was added 1 part of trimethylchlorosilane. Then 44 parts of a trimethylchlorosilane were added in a period of about 1 hour. Hydrochloride evolved and was scrubbed at the exit. With continuous stirring, the mixture was maintained at a temperature of 50°–55° C. for two hours and there was introduced a nitrogen purge for one hour. An analytical test at that point indicated that the acidity of the fluid was less than 3000 parts per million. The fluid mixture was then heated at 50° C. and the nitrogen purge was stopped. Then there was added 10 parts of trimethylorthoformate and 2 parts methanol during a period of ¼ to ½ hour, some gassing and refluxing occurred and the mixture was heated at 50° to 55° C. for 1 hour and the nitrogen purge was utilized for 1 hour and the mixture was heated to 70° C. for 1 hour. The mixture heating at 70° C. was continued until the acidity of the fluid was below 50 parts per million of acid. Then the fluid was vacuum stripped at about 50 mm or less using a nitrogen purge and heating to no more than 240° C. When no volatiles were evident using the vapor temperature, the batch was cooled in a nitrogen atmosphere and the acidity and the volatiles determination were carried out. The volatiles determination showed that the amount of the volatiles was below 2 percent. Accordingly, at this point, the stripping operation was terminated and there resulted the desired trimethylsiloxane end-stopped dimethylpolysiloxane dimethyl 3,3,3-trifluoropropyl polysiloxane fluid having a viscosity of 950 to 1050 centipoise at 77° F., the fluid had an acidity of 0 to 3 parts per million of HCL and a specific gravity of 1.27.

EXAMPLE 2

To 300 parts of diphenyldimethoxysilane containing 5000 ppm acidic chloride (calculated as HCL) there is added a mixture of 8 parts of trimethylorthoformate and 2 parts of methyl alcohol. The mixture is stirred at 75° C. for one hour and then is stripped at atmospheric pressure to a pot temperature of 170° C. The cool, clear residue contains less than 10 ppm acidic chloride (calculated at HCL).

EXAMPLE 3

A silanol-terminated linear polydimethylsiloxane (500 parts) having a viscosity of 2500 cps at 25° C. and an acidic chloride content of more than 1500 ppm (calculated as HCL) is treated with a mixture of 15 parts of trimethylorthoformate and 4 parts of methyl alcohol. The temperature of the stirred mixture is raised to 60° C. and then is purged with a stream of dry nitrogen for one hour. Analysis of the clear residue indicates an acidic chloride content of less than 50 ppm (calculated as HCL). After the residue is stripped at 20 mm pressure to a temperature of 150° C. it has an acidic chloride content of less than 10 ppm (calculated as HCL).

EXAMPLE 4

A methoxy-terminated linear polydimethylsiloxane (400 parts) with a viscosity of 525 cps. at 25° C. and an acidic chloride content of more than 1000 ppm (calculated as HCL) is prepared by the reaction of trimethylorthoformate and a chlorodimethylsilyl-terminated polydimethylsiloxane. This methoxy-terminated polymer is heated with stirring to 80° C. Then a mixture of 10 parts of trimethylorthoformate and 2 parts of methyl alcohol is added and the mixture is stirred for one hour. Next a purge of dry nitrogen is passed through the clear mixture for one hour. The residue is then stripped at 120° C. and 50 mm pressure to yield a clear residue containing less than 10 ppm acidic chloride (calculated as HCL).

EXAMPLE 5

A trimethylsilyl-terminated linear polydimethylsiloxane (300 parts) which is prepared by the reaction of trimethylchlorosilane and a silanol-terminated polydimethylsiloxane has an acidic chloride content of more than 2000 ppm (calculated as HCL). To this polymer is added 6 parts of trimethylorthoformate and 1 part of methyl alcohol and the mixture is heated at 65° C. with stirring for one hour. The polymer is then stripped at 15 mm pressure and 100° C. for one hour. The clear residue has an acidic chloride content of less than 10 ppm (calculated as HCL).

I claim:

1. A method of neutralizing a halogen silicone compound comprising adding to the halogen silicone compound from 1 to 5 moles per mole of the halogen silicone compound selected from the class consisting of halo silanes and siloxanes of a formate of the formula,

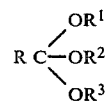

where R is selected from the class consisting of halogen and alkyl radicals of 1 to 3 carbon atoms and $R^1$, $R^2$, $R^3$ may be the same or different and is an alkyl radical of 1 to 8 carbon atoms and from 0.05 to 1 mole based on 1 mole of said halogen silicone compound of an aliphatic alcohol having 1 to 6 carbon atoms.

2. The process of claim 1 further comprising after the neutralization of the halogen silicone compound is complete; distilling off all excess formate and aliphatic alcohol as well as the neutralization by-product compound.

3. The process of claim 2 wherein in said distilling step the temperature of 240° C. is not exceeded.

4. The process of claim 3 wherein that halogen silicone compound is a chlorosilane.

5. The process of claim 4 wherein before the neutralization step further comprising reacting a cyclotrisiloxane of the formula, $$(R^5R^6SiO)_3$$

with small amounts of water to produce a silanol end-stopped diorganopolysiloxane of a viscosity varying from 50 to 1,000,000 centipoise at 25° C. where $R^5$ is a monovalent hydrocarbon radical $R^6$ is trifluoropropyl and the organo group is selected from $R^5$ and $R^6$ radicals and then reacting the silanol end-stopped diorganopolysiloxane with a triorganochlorosilane compound where the organo group in said triorganochlorosilane is selected from the same groups as $R^5$ $R^6$ to produce a triorganosilyl end-stopped diorganopolysiloxane from 50 to 1,000,000 centipoise viscosity with excess chlorosiloxane compound in the reaction mixture.

6. The process of claim 5 wherein the triorganochlorosilane has the formula, $$R_3^7SiCl$$

where $R^7$ is a monovalent hydrocarbon radical.

7. The process of claim 6 wherein where the cyclotrisiloxanes are reacted with water and wherein there is present as a promotor a polyethylene glycol dimethyl ether promotor and as a catalyst an alkali metal hydroxide.

8. The process of claim 7 wherein in the reaction of the cyclotrisiloxane with water after the reaction is complete the catalyst is neutralized with triorganochlorosilane and reaction is carried out at 25° C. to 100° C.

9. The process of claim 8 wherein 1 mole of said silanol end-stopped diorganopolysiloxane is reacted with at least 2 moles of said triorganochlorosilane at a temperature of 0° to 100° C. for a period of time varying from 1 to 6 hours.

10. The process of claim 9 wherein said formate and aliphatic alcohol are trimethylorthoformate and methanol.

11. The process of claim 10 wherein said formate and aliphatic alcohol are reacted with said chlorosilane compound at 0° to 100° C.

12. The process of claim 11 wherein said formate and aliphatic alcohol are reacted with said chlorosilane at atmospheric pressure for 1 to 6 hours.

13. The process of claim 12 wherein said formate and aliphatic alcohol are reacted with said chlorosilane at 50° to 100° C. temperature.

14. A process for neutralizing a fluorosiloxane polymer having chlorosilanes intimately mixed with the polymer comprising (1) reacting a cyclotrisiloxane of the formula, ps $$(R^5R^6SiO)_3$$

with small amounts of water in the presence of an alkali metal hydroxide and as a promoter a polyethyleneglycol dimethyl ether at a temperature of 25° C. to 100° C. to provide a silanol end-stopped diorganopolysiloxane of a viscosity varying from 50 to 1,000,000 centipoise at 250° C. where $R^5$ is monovalent hydrocarbon radical, $R^6$ is trifluoropropyl and the organo groups are selected from $R^5$ and $R^6$ radicals; (2) adding to the silanol end-stopped diorganopolysiloxane a triorganochlorosilane of the formula, $$R_3^7SiCl$$

where $R^7$ is a monovalent hydrocarbon radical at a temperature of 0° to 100° C. for 1 to 6 hours; and (3) neutralizing the excess chlorosilane by adding from 1 to 5 moles of methylorthoformate and 0.05 to 1 mole of methanol per mole of said excess chlorosilane at a temperature of 50° to 100° C.; and (4) distilling off the excess methylorthoformate, methanol and the neutralization by-product where the temperature of the distillation does not exceed 240° C.

* * * * *